United States Patent [19]

Nakagawa et al.

[11] 4,325,968
[45] Apr. 20, 1982

[54] BENZENETHIOCARBAMATE DERIVATIVES

[75] Inventors: Taizo Nakagawa, Ageo; Yutaka Watanabe, Saitama; Kaoru Ohmori, Okegawa; Kengo Koike, Ageo; Iwao Tejima, Yono, all of Japan

[73] Assignee: Nippon Kayaku Kabushiki Kaisha, Tokyo, Japan

[21] Appl. No.: 222,572

[22] Filed: Jan. 5, 1981

[30] Foreign Application Priority Data

Jan. 23, 1980 [JP] Japan ................... 55-5664

[51] Int. Cl.³ .................. A01N 47/10; C07C 155/02
[52] U.S. Cl. ................ 424/300; 260/455 A; 71/100
[58] Field of Search ........... 260/455 A; 424/300; 71/100

[56] References Cited

U.S. PATENT DOCUMENTS 3,450,745  6/1969  Payne et al. ............. 260/455 A
4,183,957  1/1980  Pawloski ................. 424/300
4,200,632  4/1980  Nakagawa ............... 424/300

Primary Examiner—John M. Ford
Assistant Examiner—Robert C. Whittenbaugh
Attorney, Agent, or Firm—Henry C. Nields

[57] ABSTRACT

Compounds represented by the formula:

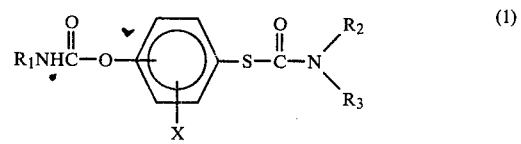

Wherein $R_1$ is alkyl having 1 to 4 carbon atoms, $R_2$ is hydrogen or alkyl having 1 to 4 carbon atoms, $R_3$ is alkyl having 1 to 4 carbon atoms and X is hydrogen, halogen, alkyl having 1 to 4 carbon atoms, alkoxy having 1 to 4 carbon atoms or alkylsulfonyloxy having 1 to 4 carbon atoms, and preparation methods thereof, and use thereof as a fungicide and for regulating the growth of plants.

17 Claims, No Drawings

BENZENETHIOCARBAMATE DERIVATIVES

DETAILED DESCRIPTION OF THE INVENTION

The present invention relates to benzenethiocarbamate derivatives represented by the formula:

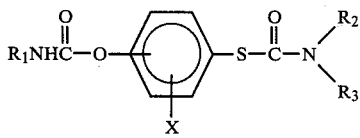

Wherein $R_1$ is alkyl having 1 to 4 carbon atoms, $R_2$ is hydrogen or alkyl having 1 to 4 carbon atoms, $R_3$ is alkyl having 1 to 4 carbon atoms and X is hydrogen, halogen, alkyl having 1 to 4 carbon atoms, alkoxy having 1 to 4 carbon atoms or alkylsulfonyloxy having 1 to 4 carbon atoms, and preparation methods thereof, a soil fungicidal composition and a plant growth regulating composition comprising one or more of said derivatives as an active ingredient, a method for preventing soil-borne plant diseases caused by fungi and further to a method for regulating the growth of plants.

Heretofore, the prevention of soil-borne plant diseases was very difficult and development of a good fungicide has been desired. There has been especially awaited a fungicide which can prevent different types of disease attacking various kinds of agricultural and horticultural plants and yet is free of phytotoxicity.

The inventors have eagerly undertaken researches to develop a soil fungicide and have found the fact that the compounds of the formula (1) show a wide-ranged and very high prevention effect against different soil-borne plant diseases, especially having an excellent effect against such soil-borne plant diseases caused by fungus as rice blast, damping-off of cucumber, phytophthora rot of cucumber, fusarium wilt of cucumber, stem rot of pepper, verticillium wilt of tomato, clubroot of cabbage and Chinese cabbage, and the like, without causing any phytotoxicity.

It has also been found that the compounds of the formula (1) work not only as a soil fungicide but also as a plant growth regulator which is effective to regulate the growth of usueful plants when said compounds are applied to said plants or soil, for example to accelerate rooting of rice seedlings.

In the compounds of formula (1) of the present invention, there can be used for example chloro and bromo as halogen, methyl, ethyl, propyl and butyl as alkyl having 1 to 4 carbon atoms, methoxy, ethoxy, propoxy and butoxy as alkoxy having 1 to 4 carbon atoms, and methanesulfonyloxy, ethanesulfonyloxy, propanesalfonyloxy and butanesulfonyloxy as alkylsulfonyloxy having 1 to 4 carbon atoms.

Preferred compounds of the formula (1) are those wherein $R_1$ is methyl, $R_2$ is methyl, $R_3$ is hydrogen and X is hydrogen, chloro, bromo, alkyl having 1 to 4 carbon atoms, alkoxy having 1 to 4 carbon atoms or alkylsulfonyloxy having 1 to 4 carbon atoms, and especially preferable are those wherein $R_1$ is methyl, $R_2$ is methyl, $R_3$ is hydrogen and X is hydrogen, chloro, methyl, methoxy or methylsulfonyloxy. The compounds of the present invention represented by the formula (1) are prepared by the processes described in method A or method B below.

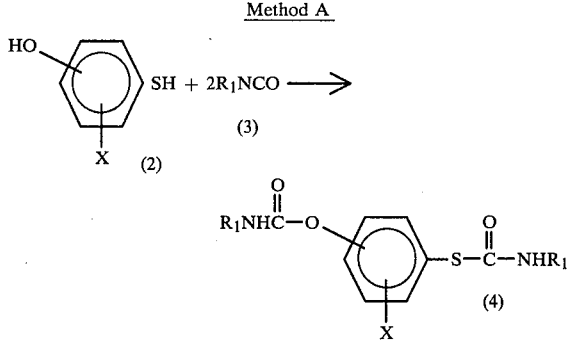

(wherein $R_1$ and X are as defined above.)

According to the above reaction formula a substituted hydroxybenzenethiol of formula (2) is dissolved in an inert organic solvent, a lower alkylisocyanate of formula (3) is added thereto and the reaction is carried out for an hour to several hours at a temperature between room temperature and the boiling point of the inert organic solvent used. Thus there can be obtained a substituted O,S-bis-N-alkyl-benzenethiocarbamate of formula (4). The reaction will be accelerated if a suitable catalyst such as triethylamine is added to the extent of 0.01 to 0.1 percent of the weight of a substituted hydroxybenzenethiol represented by the formula (2).

Such a known substituted hydroxybenzenethiol used as a raw material can be prepared in the following way. A hydroxyl group is protected with benzoyl group to form the corresponding substituted benzoyloxybenzenesulfochloride and the resulting substance is reduced by such a known method as given on page 504 or Organic Synthesis Collective Volume I, or otherwise one may adopt a method described in U.S. Pat. No. 3,952,064 or U.S. Pat. 3,781,367.

As a lower alkylisocyanate of the formula (3) there can be used methylisocyanate, ethylisocyanate, propylisocyanate, butylisocyanate or others.

An inert organic solvent used in said reaction includes aliphatic or aromatic hydrocarbons and their halogen substitutive derivatives such as chloroform, carbon tetrachloride, cyclohexane, toluene, xylene, benzene and chlorobenzene, ketones such as acetone, methylethylketone and methylbutylketone, aliphatic nitriles such as acetonitrile and propionitrile, ethers such as diethylether, tetrahydrofurane and dioxane, and others.

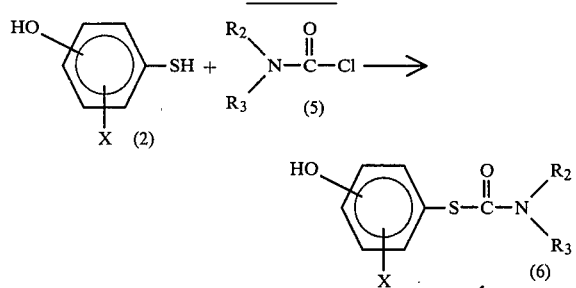

-continued
Method B

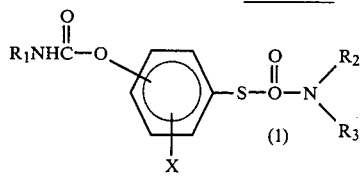

(wherein R₁, R₂, R₃ and X are as defined above)

A substituted hydroxybenzenethiol of the formula (2) is reacted with an N-alkylcarbamoylchloride of the formula (5) in an inert organic solvent using a suitable base as a condensing agent at a temperature between room to temperature and the boiling point of the solvent used and there is obtained a compound of the formula (6).

Examples of the base used as a condensing agent, are aliphatic, aromatic or heterocyclic tertiary bases such as triethylamine, dimethylaniline, pyridine and picoline, alkali metal carbonates and bicarbonates such as sodium carbonate, potassium carbonate and sodium bicarbonate, general strong bases such as sodium hydroxide, potassium hydroxide and calcium hydroxide, and others. Preferably organic bases such as pyridine, picoline and dimethylamine are used.

The preparing methods of the compounds of the present invention will be illustrated in the following synthesis examples.

SYNTHESIS EXAMPLE 1

2-methyl-5-N-methylcarbamoyloxyphenyl-N-methyl-thiocarbamate (Compound No. 6)

5.0 g (0.0357 mole) of 2-methyl-5-hydroxybenzenethiol and 4.1 g (0.071 mole) of methylisocyanate were dissolved in 40 cc of benzene, 2 drops of triethylamine were added thereto, and the mixtures was allowed to stand for a while at room temperature. Then the reaction mixture was concentrated under reduced pressure and the resulting crude crystals were recrystallized by using a small amount of benzene to obtain 7.6 of white crystals.

Yield: 83.6%. Melting point: 140°–141° C.

SYNTHESIS EXAMPLE 2

3-N-methylcarbamoyloxyphenyl-N,N-dimethylthiocarbamate (Compound No. 7)

5.8 g (0.05 mole) of 3-hydroxybenzenethiol, 10.8 g (0.1 mole) of N,N-dimethylcarbamoylchloride and 4.7 g (0.55 mole) of pyridine were dissolved in 50 cc of ethylether and the mixture was stirred under reflux for 10 to 15 hours. The reaction mixture was concentrated under reduced pressure and the resulting crude crystals were washed with water followed by recrystallization from a small amount of ethyl acetate to obtain 5.0 g of white crystals of 3-hydroxyphenyl-N,N-dimethylthiocarbamate.

Yield: 50.7%. Melting point: 140°–141° C.

5.0 G (0.025 mole) of 3-hydroxyphenyl-N,N-dimethylthiocarbamate obtained as above and 1.6 g (0.028 mole) of methylisocyanate were dissolved in 30 cc of acetonitrile, 1 drop of triethylamine was added thereto and the mixture was stirred under reflux for an hour. The reaction mixture was concentrated under reduced pressure and the resulting crude crystals were recrystallized from a small amount of ethyl acetate to obtain 4.5 g of white crystals.

Yield: 75.0%. Melting point: 147°–150° C.

SYNTHESIS EXAMPLE 3

2-N-methylcarbamoyloxy-5-methanesulfonyloxy-N-methylthiocarbamate (Compound No. 14)

11.0 g (0.05 mole) of 2-hydroxy-5-(methanesulfonyloxy)benzenethiol and 6.3 g (0.11 mole) of methylisocyanate were dissolved in 50 cc of tetrahydrofurane, 3 drops of triethylamine were added thereto and the mixture was allowed to stand at room temperature for a while. After confirming the completion of the reaction by thin layer chromatography, the reaction mixture was concentrated under reduced pressure and the resulting crude crystals were recrystallized from a small amount of ethyl acetate to obtain 14.9 g of white crystals.

Yield: 89.3%. Melting point: 108°–110° C.

The typical compounds of the present invention prepared by the procedures described above are shown in Table 1.

TABLE 1

| Compound No. | Formula | Physical property | Preparation method |
|---|---|---|---|
| 1. | (structure: phenyl with O-C(=O)-NHCH₃, S-C(=O)-NHCH₃, Cl) | mp. 119.5–120.5° C. | A |
| 2. | (structure: phenyl with O-C(=O)-NHCH₃, S-C(=O)-NHCH₃, OCH₃) | mp. 125–126° C. | A |
| 3. | (structure: phenyl with O-C(=O)-NHC₄H₉(n), S-C(=O)-NHC₄H₉(n), Cl) | mp. 125.5–126.5° C. | A |

TABLE 1-continued

| Compound No. | Formula | Physical property | Preparation method |
|---|---|---|---|
| 4. | 4-Cl-phenyl with O-C(=O)-NHCH₃ and S-C(=O)-N(CH₃)₂ substituents | mp. 128–129° C. | B |
| 5. | phenyl with O-C(=O)-NHCH₃ and S-C(=O)-NHCH₃ | mp. 157–160° C. | A |
| 6. | methylphenyl with O-C(=O)-NHCH₃ and S-C(=O)-NHCH₃, CH₃ | mp. 140–141° C. | A |
| 7. | phenyl with O-C(=O)-NHCH₃ and S-C(=O)-N(CH₃)₂ | mp. 147–150° C. | B |
| 8. | phenyl with O-C(=O)-NHC₃H₇(n) and S-C(=O)-NHC₃H₇(n) | mp. 127.5–129° C. | A |
| 9. | CH₃NHC(=O)-O—⟨phenyl⟩—S-C(=O)-NHCH₃ | mp. 111–112° C. | A |
| 10. | CH₃NHC(=O)-O—⟨phenyl⟩—S-C(=O)-N(C₂H₅)₂ | mp. 122–124° C. | B |
| 11. | C₂H₅NHC(=O)-O—⟨phenyl⟩—S-C(=O)-NHC₂H₅ | mp. 157–158° C. | A |
| 12. | (n)C₃H₇NHC(=O)-O—⟨phenyl⟩—S-C(=O)-NHC₃H₇(n) | mp. 126–127° C. | A |
| 13. | (n)C₃H₇NHC(=O)-O—⟨phenyl⟩—S-C(=O)-N(C₂H₅)₂ | mp. 143–145° C. | B |
| 14. | CH₃SO₂O—⟨phenyl⟩ with SCONHCH₃ and OCONHCH₃ | mp. 108–110° C. | A |
| 15. | CH₃SO₂O—⟨phenyl⟩ with SCONHC₄H₉(n) and OCONHC₄H₉(n) | mp. 90.5–91° C. | A |
| 16. | ⟨phenyl⟩ with SCONHCH₃, OCONHCH₃ and H₃CO₂SO | mp. 108–110° C. | A |

TABLE 1-continued

| Compound No. | Formula | Physical property | Preparation method |
|---|---|---|---|
| 17. | 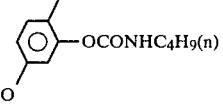 | mp. 90.5-91° C. | A |

The compounds of the present invention are used as a soil fungicide or a plant growth regulant in various types of formulation. Though the compounds may be used along occasionally, they are usually mixed with one or more of adjuvants suc as carries, extending agents, emulsifiers, wetting agents, dispersing agents, fixing agents and disintegrators to use in the forms such as emulsion, wettable powder, dust, granule and micro granule in compliance with the requirement of the purposes. In practical application, these types of formulation are used as they are or can be used after dilution with water to proper concentration.

As carriers both solid and liquid ones can be used. Solid carriers include clay, kaolin, talc, diatomaceous earth, silica, calcium carbonite, montmorillonite, bentonite, feldspar, quartz, alumina, etc. and liquid carriers include fraction products of oil such as kerosene and light oil, aromatic hydrocarbons such as toluene and xylene, methylnaphthalene, cyclohexane, alcohols such as methanol, butanol and glycol, acetone, amides such as dimethylformamide, sulfoxides such as dimethylsulfoxide, animal and vegetable oils, fatty acides and their esters, etc. Other adjuvants such as extending agents, emulsifiers, wetting agents, dispersing agents, fixing agents and disintegrators are used in order to assure the effects of the active ingredient. There are used for example polyoxyethylenealkylphenolether and higher alcohol ester as an extending agent and a wetting agent, casein and sodium alginate as a fixing agent, and carboxymethylcellulose sodium salt and gum arabic as disintegrator.

As an emulsifier and dispersing agent surfactants are generally used. And surfactants include anionic, cationic, nonionic and amphoteric surfactants such as higher alcohol sodium sulfate, steariltrimethylammonium chloride, polyoxyethylenealkylphenylether and lauryl betaine.

The content of a compound of the formula (1) in the formulations is satisfactory with the same as that of an active ingredient in conventional formulations, that is 0.5 to 95%, preferably 2 to 70%, while the content of adjuvants is 5 to 99.5%, preferably 30 to 98%. And preferable content can be given differently for respective types of formulation. For example, in the case of dust, the content of a compound of the formula (1) is 0.5 to 20% that of adjuvants being 80 to 99.5%, while in wettable powder the compound is 20 to 80%, adjuvants being 20 to 80% and in granule and micro granule the compound is 2 to 10% adjuvants being 90 to 98%.

Regardless of types, any formulation of the compound (1) can be used by itself and may also be blended with fungicides, herbicides, plant growth regulating compositions, acaricides, insecticides, soil modifying agents or nematocides, furthermore available for mixture with fertilizers or other soil fungicides.

Further detailed explanation is given on formulations of the present invention in the following examples, but the kinds of the additives and the mixing ratios are not limited within the range of those examples below and can be applicable more freely in wider ranges.

In the following examples "part" means part by weight.

Formulation Example 1: Dust 10 parts of the compound No. 1 of the present invention (3-chloro-6-N-methylcarbamoyloxyphenyl-N-methylthiocarbamate), 41 parts of talc and 49 parts of clay were mixed and pulverized to obtain a dust.

Formulation Example 2: Wettable powder 80 parts of the compound No. 5 of the present invention (3-N-methylcarbamoyloxyphenyl-N-methylthiocarbamate), 15 parts of kaolin, 3 parts of sodium higher alcohol sulfate and 2 parts of sodium polyacrylate were mixed and pulverized to obtain a wettable powder.

Formulation Example 3: Granule 3 parts of the compound No. 6 of the present invention (2-methyl-5-N-methylcarbamoyloxyphenyl-N-methylthiocarbamate), 35 parts of diatomaceous earth, 23 parts of bentonite, 37 parts of talc and 2 parts of disintegrator were mixed, 18 parts of water were added to moisten the mixture homogeneously and then extruded through an injection molding machine to make granules, which were dried and submitted to a comminutor to obtain granules having a particle size of 0.6 to 1 mm.

Formulation Example 4: Micro granule 5 parts of the compound No. 9 of the present invention (4-N-methylcarbamoyloxyphenyl-N-methylthiocarbamate), 6 parts of bentonite and 9 parts of clay were homogeneously mixed and pulverized to make a concentrated powder mixture. Separately 80 parts of non-absorbent coarse mineral powder of 74 to 105 micron size were placed in a proper mixing machine, to which were added 20 parts of water to moisten while rotating the machine and further said concentrated powder mixture to coat, and then dried to obtain micro granules. The effects of the present invention are shown in the following test examples.

TEST EXAMPLE 1

Exterminating test on rice blast (fungi: Rhizopus)

A nursery box sized 60 cm×30 cm×3 cm was filled with soil and uniformly inoculated with 500 g per box of soil in which were cultured the pathogenic fungi of said disease (*Rhizopus chinensis*). After that, the soil was uniformly mixed up with a given amount of a dust of the compound of the present invention prepared by the procedure as given in the Formulation Example 1.

Then the seeds of rice (variety: Nihonbare) were sowed at the rate of 0.3 l per box and nursed in a moist chamber at 33° C. for 3 days, followed by placing in a greenhouse for another 3 days keeping the temperature at 25° C. by day and 20° C. by night and thereafter left to stand in a greenhouse kept at 20° C. by day and 15° C. by night for 11 days.

A dust containing 4% of TPN (active ingredient: tetrachloroisophthalonitrile) was used as a control and tested in the same way as mentioned above. 15 days after sowing the percentage of healthy seedlings was calculated as follows:

Percentage of healthy seedlings (%) = $\dfrac{\text{number of healthy seedlings}}{\text{number of observed seedlings}} \times 100$ The results are shown in Table 2.

TABLE 2

| Compound No. | | Active ingredient quantity | Percentage of healthy seedling | Phytotoxicity |
|---|---|---|---|---|
| Present invention | 1 | 0.8 g/box | 94.2% | None |
| | 2 | 0.8 g/box | 93.7% | None |
| | 3 | 0.8 g/box | 95.8% | None |
| | 4 | 0.8 g/box | 96.3% | None |
| | 5 | 0.8 g/box | 91.0% | None |
| | 6 | 0.8 g/box | 93.2% | None |
| | 7 | 0.8 g/box | 75.4% | None |
| | 9 | 0.8 g/box | 98.2% | None |
| Control | Dust containing 4% TPN | 0.8 g/box | 72.4% | None |
| | Blank | — | 10.5% | — |

TEST EXAMPLE 2

Exterminating test on rice blast (fungi: Fusarium)

A nursery box sized 60 cm×30 cm×3 cm was filled with soil and uniformly inoculated with 200 g per box of soil in which were cultured the pathogenic fungi of said disease (*Fusarium roseum*). Therefore, a wettable powder of the compound of the present invention prepared by the procedure as given in the Formulation Example 2 was diluted with water and drenched at the rate of 500 ml per box. Then the seeds of rice (variety: Nihonbare) were sown at the rate of 0.3 l per box and nursed in an inoculation box kept at 32° C. for 3 days, left to stand in a greenhouse kept at 25° C. by day and 20° C. by night for 3 days and next in a room maintained at 3° to 5° C. for another 3 days, lastly transferred again to a greenhouse kept at 20° C. by day and 15° C. by night and 9 days after the sawing the results were examined. A solution containing 30% of hydroxyisooxazole (active ingredient: 3-hydroxy-5-methylisooxazole) was used as control and tested in the same way as mentioned above.

The results are shown in Table 3 giving the percentage of healthy seedlings.

TABLE 3

| Compound No. | | Active ingredient quantity | Percentage of healthy seedling | Phytotoxicity |
|---|---|---|---|---|
| Present invention | 1 | 800 ppm | 92.4% | None |
| | 2 | 800 ppm | 93.8% | None |
| Control | A solution containing 30% hydroxy-isoxazol | 800 ppm | 86.5% | None |
| | Blank | — | 43.2% | — |

TEST EXAMPLE 3

Exterminating test on damping-off of cucumber seedling

A pot of 12 cm diameter was filled with field soil and the soil surface was uniformly inoculated with 5 g per pot of soil in which were cultured the pathogenic fungi of said disease (*Pythium ultimum*). After that, 3 cm thick soil of the uppermost layer was uniformly mixed with a given amount of a dust of the compound of the present invention prepared by the procedure as given in the Formulation Example 1.

Then the seeds of cucumber (variety: Ohyashima) were sowed at the rate of 10 seeds per pot. The attacking by the disease was made in a greenhouse.

A dust containing 4% of ecromezol (active ingredient: 5-ethoxy-3-trichloromethyl-1,2,4-thiadiazole) was used as a control and tested in the same way as mentioned above.

14 days after sowing, the degree of attack by pathogen was obserbed and the percentage of healthy seedlings was calculated as follows:

Percentage of healthy seedlings (%) = $\dfrac{\text{Number of healthy seedlings in each treated pot}}{\text{Number of germination in untreated and uninoculated pot}} \times 100$ The results are shown in Table 4.

TABLE 4

| Compound No. | | Active ingredient quantity | Percentage of healthy seedling | Phytotoxicity |
|---|---|---|---|---|
| Present invention | 2 | 0.01 g/pot | 95% | None |
| | 4 | 0.01 g/pot | 98% | None |
| | 5 | 0.01 g/pot | 90% | None |
| | 9 | 0.01 g/pot | 94% | None |
| | 11 | 0.01 g/pot | 92% | None |
| Control | Dust containing 4% Ecromezol | 0.01 g/pot | 90% | None |
| | Blank | — | 0 | — |

TEST EXAMPLE 4

Extermination test on fusarium wilt of cucumber

A pot of 18 cm diameter was filled with field soil and therewith are mixed for inoculation 20 g per pot of soil on which were cultured the pathogenic fungi of said disease (*Fusarium oxysporum f. cucumerinum*).

After that, the seeds of cucumber (variety: Tokiwajibae) were sowed at the rate of 18 seeds per pot and then a wettable powder of the compound of the present invention prepared by the procedure as given in the Formulation Example 2 was diluted with water and drenched at the rate of 100 ml per pot. The attacking by the disease was made in a greenhouse.

A wettable powder containing 50% of benomyl (active ingredient: methyl-1-(butylcarbamoyl)-2-benzimidazolecarbamate) was used as a control and tested in the same way as mentioned above.

2 weeks after sowing, the degree of attack by the pathogen was observed and the percentage of healthy seedlings was calculated in the same way as described in Test Example 3. The results are shown in Table 5.

TABLE 5

| Compound No. | | Active ingredient quantity | Percentage of healthy seedling | Phytotoxicity |
| --- | --- | --- | --- | --- |
| Present invention | 1 | 1,000 ppm | 95% | None |
| | 2 | 1,000 ppm | 92% | None |
| | 3 | 1,000 ppm | 90% | None |
| | 6 | 1,000 ppm | 88% | None |
| | 14 | 1,000 ppm | 92% | None |
| | 15 | 1,000 ppm | 90% | None |
| Control | Wettable powder containing 50% Benomyl | 1,000 ppm | 85% | None |
| Blank | | — | 15% | — |

As known from Test Examples 1 to 4, the compounds of the present invention show excellent prevention effect against different types of diseases which appear on various crops. On the contrary, those compounds used as a control in respective Test Examples are effective only against the disease of their corresponding Test Examples. Moreover, in the cases of Test Examples No. 1 and 4, the control is inferior to the compounds of the present invention in efficacy.

TEST EXAMPLE 5

Extermination test on promotion of rooting of rice seedling

A nursery box sized 60 cm×30 cm×3 cm was filled with soil and the soil was uniformly mixed with a given amount of a dust of the compound of the present invention prepared in the same way as given in Formulation Example 1. Then seeds of rice (variety: Nihonbare) were sowed at the rate of 0.3 l per box and after nursing at 30° C. for 3 days, they were left to stand for 3 days in a greenhouse kept at 25° C. by day and 20° C. by night and afterwards in a greenhouse kept at 20° C. by day and 15° C. by night. 20 days after sowing, the seedlings were taken up and roots were cut with scissors. Then the seedlings were raised in water for 5 days, and the length of regenerating roots and the number were observed.

The results are shown in Table 6.

TABLE 6

| Compound No. | | Active ingredient quantity | The longest root (cm) | Number of root |
| --- | --- | --- | --- | --- |
| Present invention | 1 | 10 g/box | 3.5 | 3.8 |
| | 2 | 10 g/box | 2.9 | 2.4 |
| Blank | | — | 1.8 | 1.4 |

What we claim is:

1. A compound represented by the formula:

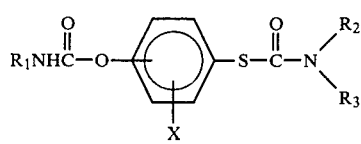

wherein $R_1$ is alkyl having 1 to 4 carbon atoms, $R_2$ is hydrogen or alkyl having 1 to 4 carbon atoms, $R_3$ is alkyl having 1 to 4 carbon atoms, X is hydrogen, halogen, alkyl having 1 to 4 carbon atoms, alkoxy having 1 to 4 carbon atoms or alkylsulfonyloxy having 1 to 4 carbon atoms.

2. The compound according to claim 1 wherein $R_1$ is methyl, $R_2$ is methyl, $R_3$ is hydrogen and X is hydrogen, chloro, bromo, alkyl having 1 to 4 carbon atoms, alkoxy having 1 to 4 carbon atoms or alkylsulfonyloxy having 1 to 4 carbon atoms.

3. The compound according to claim 1 wherein $R_1$ is methyl, $R_2$ is methyl, $R_3$ is hydrogen and X is hydrogen, chloro, methyl, methoxy or methylsulfonyloxy.

4. A soil fungicidal composition comprising 0.5~95% by weight of one or more compounds of the formula:

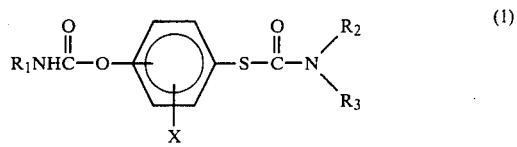

wherein $R_1$ is alkyl having 1 to 4 carbon atoms, $R_2$ is hydrogen or alkyl having 1 to 4 carbon atoms, $R_3$ is alkyl having 1 to 4 carbon atoms, X is hydrogen, halogen, alkyl having 1 to 4 carbon atoms, alkoxy having 1 to 4 carbon atoms or alkylsulfonyloxy having 1 to 4 carbon atoms and 99.5 to 0.5% by weight of adjuvants.

5. The soil fungicidal composition according to claim 4 wherein $R_1$ is methyl, $R_2$ is methyl, $R_3$ is hydrogen and X is hydrogen, chloro, bromo, alkyl having 1 to 4 carbon atoms, alkoxy having 1 to 4 carbon atoms or alkylsulfonyloxy having 1 to 4 carbon atoms.

6. The soil fungicial composition according to claim 4 wherein $R_1$ is methyl, $R_2$ is methyl, $R_3$ is hydrogen and X is hydrogen, chloro, methyl, methoxy or methylsulfonyloxy.

7. A plant growth stimulating composition comprising 0.5~95% by weight of one or more compounds represented by the formula:

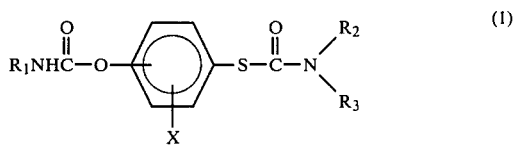

wherein $R_1$ is alkyl having 1 to 4 carbon atoms, $R_2$ is hydrogen or alkyl having 1 to 4 carbon atoms, $R_3$ is alkyl having 1 to 4 carbon atoms, X is hydrogen, halogen, alkyl having 1 to 4 carbon atoms, alkoxy having 1 to 4 carbon atoms or alkylsulfonyloxy having 1 to 4 carbon atoms.

8. The plant growth stimulating composition according to claim 1 wherein $R_1$ is methyl, $R_2$ is methyl, $R_3$ is hydrogen and X is hydrogen, chloro, bromo, alkyl having 1 to 4 carbon atoms, alkoxy having 1 to 4 carbon atoms or alkylsulfonyloxy having 1 to 4 carbon atoms.

9. The plant growth stimulating composition according to claim 7 wherein $R_1$ is methyl, $R_2$ is methyl, $R_3$ is hydrogen and X is hydrogen, chloro, methyl, methoxy or methylsulfonyloxy.

10. A method for preventing soil borne plant disease caused by fungi which comprises treating soil containing the fungi with an effective amound of compound represented by the formula:

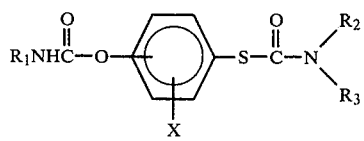 (1)

wherein $R_1$ is alkyl having 1 to 4 carbon atoms, $R_2$ is hydrogen or alkyl having 1 to 4 carbon atoms, $R_3$ is alkyl having 1 to 4 carbon atoms, X is hydrogen, halogen, alkyl having 1 to 4 carbon atoms, alkoxy having 1 to 4 carbon atoms or alkylsulfonyloxy having 1 to 4 carbon atoms.

11. The method according to claim 10 wherein $R_1$ is methyl, $R_2$ is methyl, $R_3$ is hydrogen and X is hydrogen, chloro, bromo, alkyl having 1 to 4 carbon atoms, alkoxy having 1 to 4 carbon atoms, or alkylsulfonyloxy having 1 to 4 carbon atoms.

12. The method according to claim 7 wherein $R_1$ is methyl, $R_2$ is methyl, $R_3$ is hydrogen and X is hydrogen, chloro, methyl, methoxy or methylsulfonyloxy.

13. A method for stimulating the growth of plants which comprises applying said plant or soil the effective amount of a compound represented by the formula:

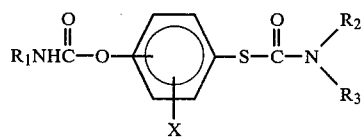 (1)

wherein $R_1$ is alkyl having 1 to 4 atoms, $R_2$ is hydrogen or alkyl having 1 to 4 carbon atoms, $R_3$ is alkyl having 1 to 4 carbon atoms, X is hydrogen, halogen, alkyl having 1 to 4 carbon atoms, alkoxy having 1 to 4 carbon atoms or alkylsulfonyloxy having 1 to 4 carbon atoms.

14. A method according to claim 13 wherein $R_1$ is methyl, $R_2$ is methyl, $R_3$ is hydrogen and X is hydrogen, chloro, bromo, alkyl having 1 to 4 carbon atoms, alkoxy having 1 to 4 carbon atoms or alkylsulfonyloxy having 1 to 4 carbon atoms.

15. The method according to claim 13 wherein $R_1$ is methyl, $R_2$ is methyl, $R_3$ is hydrogen and X is hydrogen, chloro, methyl, methoxy or methylsulfonyloxy.

16. A method for the preparation of a compound represented by the formula:

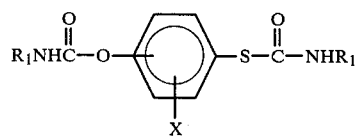 (1)

wherein $R_1$ is alkyl having 1 to 4 carbon atoms and X is hydrogen, halogen, alkyl having 1 to 4 carbon atoms, alkoxy having 1 to 4 carbon atoms or alkylsulfonyloxy having 1 to 4 carbon atoms, which comprises reacting a compound represented by the formula:

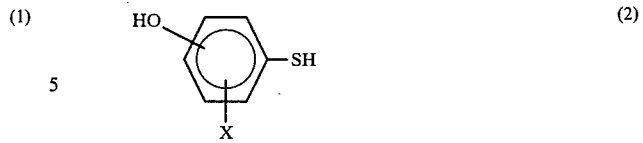 (2)

(wherein X is defined above) with a compound represented by the formula:

$R_1NCO$ (3)

wherein $R_1$ is defined above.

17. A method for the preparation of a compound represented by the formula:

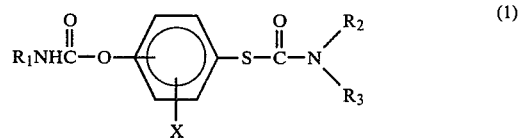 (1)

wherein $R_1$ is alkyl having 1 to 4 carbon atoms, $R_2$ is hydrogen or alkyl having 1 to 4 carbon atoms, $R_3$ is alkyl having 1 to 4 carbon atoms, X is hydrogen, halogen, alkyl having 1 to 4 carbon atoms, alkoxy having 1 to 4 carbon atoms or alkylsulfonyloxy having 1 to 4 carbon atoms, which comprises reacting a compound represented by the formula:

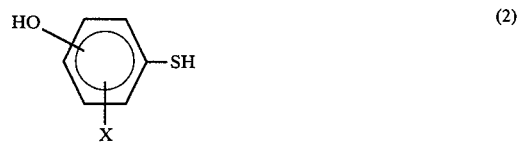 (2)

wherein X is defined above with a compound represented by the formula:

 (5)

wherein $R_2$ and $R_3$ are defined above to produce a compound represented by the formula:

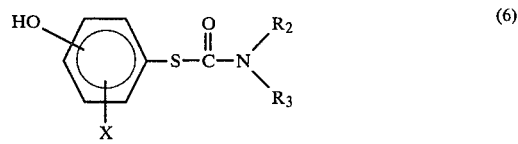 (6)

wherein $R_2$, $R_3$ and X are defined above and then reacting the compound of formula (6) with a compound represented by the formula:

$R_1NCO$ (3)

wherein $R_1$ is defined above.

* * * * *